US011504342B2

(12) United States Patent
Vasisht et al.

(10) Patent No.: US 11,504,342 B2
(45) Date of Patent: Nov. 22, 2022

(54) TRANSMUCOSAL FILM COMPOSITION AND METHODS OF MAKING AND USING THE SAME

(71) Applicant: Avior, Inc., Cary, NC (US)

(72) Inventors: Samarth Vasisht, San Francisco, CA (US); Niraj Vasisht, Cary, NC (US)

(73) Assignee: AVIOR, INC., Cary, NC (US)

( * ) Notice: Subject to any disclaimer, the term of this patent is extended or adjusted under 35 U.S.C. 154(b) by 0 days.

(21) Appl. No.: 16/971,339

(22) PCT Filed: Feb. 22, 2019

(86) PCT No.: PCT/US2019/019150
§ 371 (c)(1),
(2) Date: Aug. 20, 2020

(87) PCT Pub. No.: WO2019/165208
PCT Pub. Date: Aug. 29, 2019

(65) Prior Publication Data
US 2021/0085622 A1    Mar. 25, 2021

Related U.S. Application Data

(60) Provisional application No. 62/633,907, filed on Feb. 22, 2018.

(51) Int. Cl.
*A61K 9/70* (2006.01)
*A61K 9/00* (2006.01)
(Continued)

(52) U.S. Cl.
CPC .......... *A61K 9/7007* (2013.01); *A61K 9/0053* (2013.01); *A61K 31/485* (2013.01);
(Continued)

(58) Field of Classification Search
None
See application file for complete search history.

(56) References Cited

U.S. PATENT DOCUMENTS 9,901,545 B1    2/2018  Fuisz et al.
10,195,142 B2   2/2019  Fuisz et al.
(Continued)

FOREIGN PATENT DOCUMENTS

EP    1462095 A1    9/2004

OTHER PUBLICATIONS

EPO; Extended European Search Report for European Patent Application No. EP19757114 dated Apr. 19, 2021, 9 pages.
(Continued)

*Primary Examiner* — Melissa S Mercier
(74) *Attorney, Agent, or Firm* — NK Patent Law

(57) ABSTRACT

A pharmaceutical active-containing transmucosal delivery device comprises a polymer film comprising a polymer matrix, wherein the film has a pH in the range of about 4 to about 9, and a pharmaceutical active composition disposed on a surface of the polymer film. The composition comprises at least one pharmaceutical active ingredient in the form of particles, and wherein the particles have an average particle size of about 100 nm to about 5 microns, an anti-crystallization agent, and a pH adjusting agent, wherein the concentration of the pharmaceutical active ingredient is at least 20% w/w relative to the total weight of the pharmaceutical active composition. The delivery device exhibits a residence time in the mouth of a subject ranging from about 5 minutes to about 30 minutes and is substantially mucoadhesive to a mucosa surface when placed sublingually under the tongue or placed buccally at the inner lining of the cheek.

8 Claims, 9 Drawing Sheets

(51) Int. Cl.
*A61K 31/485* (2006.01)
*A61K 47/26* (2006.01)
*A61K 47/38* (2006.01)
*A61K 47/46* (2006.01)

(52) U.S. Cl.
CPC .............. *A61K 47/26* (2013.01); *A61K 47/38* (2013.01); *A61K 47/46* (2013.01)

(56) References Cited

U.S. PATENT DOCUMENTS

| | | | |
|---|---|---|---|
| 10,238,600 | B2 | 3/2019 | Fuisz et al. |
| 2008/0260807 | A1 | 10/2008 | Sharp |
| 2011/0129533 | A1 | 6/2011 | Straub et al. |
| 2011/0262522 | A1* | 10/2011 | Finn ................ A61P 29/02 424/444 |
| 2012/0009260 | A1* | 1/2012 | Schobel ............ A61K 9/006 514/12.3 |
| 2012/0164191 | A1* | 6/2012 | Finn ................ A61K 9/7007 424/400 |
| 2013/0045268 | A1 | 2/2013 | Finn et al. |
| 2014/0008831 | A1* | 1/2014 | Yang ................ B29C 71/02 264/40.1 |
| 2014/0271867 | A1 | 9/2014 | Myers |
| 2016/0235769 | A1* | 8/2016 | Hill .................... A61P 1/04 |
| 2017/0136078 | A1 | 5/2017 | Li et al. |
| 2021/0085622 | A1 | 3/2021 | Vasisht et al. |

OTHER PUBLICATIONS

ISA/US; International Search Report and Written Opinion for International Patent Application No. PCT/US2019/019150 dated May 31, 2019, 21 pages.
Hennequin, C., et al., "A new approach to studying inhibitors of calcium oxalate crystal growth", Urological Research, vol. 21, 1993, 8 pages.
USPTO; Non-Final Office Action for U.S. Appl. No. 16/999,192 dated Feb. 22, 2021, 20 pages.
"Alpha-Tocopheryl acetate"—Surfactant, SAAPedia [online] retrieved on Feb. 16, 2021 from: http://www.saapedia.org/en/saa/?type=detail&id=5910; 5 pages) (Year: 2021).
USPTO; Final Office Action for U.S. Appl. No. 16/999,192 dated May 25, 2021, 19 pages.
WIPO; International Preliminary Report on Patentability for International Patent Application No. PCT/US2019/019150 dated Sep. 3, 2020, 18 pages.
IPO; Office Action for Indian Patent Application No. 202017039167 dated Mar. 1, 2022, 6 pages.
USPTO; Non-Final Office Action for U.S. Appl. No. 16/999,192 dated Sep. 28, 2021, 14 pages.

* cited by examiner

Drug with fast dissolving polymer binding the drug at high concentration residing on the surface Drug free polymer matrix partially circumscribing the discrete drug domain

TRANSMUCOSAL FILM COMPOSITION AND METHODS OF MAKING AND USING THE SAME

CROSS REFERENCE TO RELATED APPLICATIONS

This application is a national stage application of International Patent Application No. PCT/US19/19150 filed on Feb. 22, 2019, which claims priority to U.S. Provisional Patent Application No. 62/633,907 filed on Feb. 22, 2018, the entire contents of each of which is incorporated herein by reference.

TECHNICAL FIELD

The presently disclosed subject matter relates to a transmucosal film composition, and to methods of making and using the disclosed composition.

BACKGROUND

Oral thin films provide a convenient way to administer pharmaceutical actives such as pharmaceutical intermediates, bioactive agents, nutraceutical products, and the like to a subject. However, such films suffer from several drawbacks. For example, current films are unsuitable for pharmaceutical actives that require high dose strengths, have poor aqueous solubility, low oral bioavailability, and/or are susceptible to enzymatic, acid, or flora destruction. Particularly, prior art films dissolve upon contact with saliva, the pharmaceutical active is swallowed, and the pharmaceutical actives enter the gastrointestinal system. Since natural bodily fluids (e.g., saliva) tend to rapidly wash away topically applied pharmaceutical active, the topical treatment of wet mucosal tissues has been problematic, particularly when fast onset of drug action, high bioavailability and significantly reduced the peak plasma concentrations of the metabolite are needed. In addition, prior art films have incorporated pastes as film protectants and as drug delivery systems. However, the film-forming behavior and bioadhesion of such pastes do not last and the product exhibits a limited residence time. Further, prior art films that include multiple layers are difficult to manufacture and are more expensive to manufacture compared to single layered films. It would therefore be beneficial to provide an improved film device that addresses the shortcomings in the prior art.

SUMMARY

In a first aspect of the invention, a pharmaceutical active-containing single layered, self-supporting, transmucosal delivery device comprises a polymer film comprising a polymer matrix, wherein the film has a pharmaceutical active composition disposed on a surface of the polymer film. The composition has a pH in a range of about 4 to about 9 and comprises at least one pharmaceutical active ingredient in the form of particles, wherein the particles have an average particle size of about 100 nm to about 5 microns. The composition further includes an anti-crystallization agent and a pH adjusting agent. The concentration of the pharmaceutical active ingredient is at least 10% w/w relative to the total weight of the pharmaceutical active composition and at least 30% w/w relative to the surface of the film composition. The delivery device exhibits a residence time in the mouth of a subject ranging from about 5 minutes to about 30 minutes and is substantially mucoadhesive to a mucosa surface when placed sublingually under the tongue or placed buccally at the inner lining of the cheek.

In the pharmaceutical active-containing transmucosal delivery device, the polymer film may comprise about 80 weight percent polymer matrix and about 10 weight percent of one or more of a permeation enhancer, pH adjusting buffer agent, taste masking agent, and flavoring agent, based on the total weight of the polymer film. In this aspect of the invention, the pH of the drug composition at the surface may be different than the pH of the polymer matrix.

The pharmaceutical active-containing transmucosal delivery device may further comprise a self-aggregating moiety, a self-assembling moiety, or both. Components of the self-aggregating or self-assembling moiety may or may not be located in the same domain of the delivery device. For example, calcium chloride can be used in combination with sodium alginate to create a self-assembling barrier gel. The calcium chloride may be a component of the pharmaceutical active composition or it may be a component of the polymer film. Similarly, the sodium alginate may be a component of the pharmaceutical active composition or it may be a component of the polymer film.

In a second aspect of the invention, a method of delivering a pharmaceutical active to a subject in need thereof comprises contacting the oral mucosa of the subject with the pharmaceutical active-containing transmucosal delivery device. In some embodiments, the subject is a human.

In a third aspect of the invention, a method of manufacturing a pharmaceutical active-containing transmucosal delivery device comprises blending a polymer matrix and a pH adjusting agent; solubilizing the blend; casting the blend into a wet polymer film; drying the polymer film; applying a pharmaceutical active composition onto a surface of the polymer film, wherein a viscosity of the composition is from about 1 cP to about 100 cP; and heating the polymer film with the pharmaceutical active composition applied thereto in order to form the pharmaceutical active-containing transmucosal delivery device.

In some embodiments, the thickness of the polymer film is greater than the thickness of the applied pharmaceutical active composition (e.g., about 500%, 750%, 1000%, 2000%, 3000%, 4000%, 5000%, 7500% or 10000% of the thickness of pharmaceutical active composition).

In some embodiments, the surface area of the polymer film is equal to or less than the surface area of the applied pharmaceutical active composition.

In some embodiments, the pharmaceutical active composition is physically inseparable from the polymer film.

In some embodiments, the polymer film is positioned directly adjacent to the pharmaceutical active composition.

In some embodiments, the local pH of the polymer film is about 4.0 to about 8.5 and the local pH of the pharmaceutical active composition is about 4 to about 9, and the pH of the two domains are different.

In some embodiments, the polymer matrix is selected from water soluble, water swellable, and/or water erodible polymers, such as (but not limited to) hydroxy propyl methyl cellulose (HPMC), methyl cellulose, hydroxyethyl cellulose (HPC), hydroxypropyl cellulose, polyvinyl pyrrolidone, sodium carboxymethyl cellulose, polyethylene oxide (PEO), pullulan, alginic acid, sodium alginate, polyethylene glycol, pectins, xanthan gum, traganeanth gum, guar gum, acacia gum, arabic gum, locust bean gum, gellan gum, polyacrylic acid, polyacrylic acid cross-lined with divinyl glycol, methyl methacrylate copolymer, carboxy vinyl copolymers, natural and hydrolyzed starch, gelatin type A and B, carrageenan, or combinations thereof.

In some embodiments, the polymer film comprises about 10 to about 90 weight percent polymer matrix, based on the total weight of the film.

In some embodiments, the permeation enhancer is selected from one or more lipophilic solvents, surfactants, menthols, fatty acid esters, and polyhydric alcohols.

In some embodiments, the buffer or pH adjusting agent is selected from one or more of phosphate, acetate, citrate, arginine, TRIS, and histidine buffers.

In some embodiments, the taste masking agent is selected from cellulose acetate, cellulose acetate butyrate, ethyl cellulose, methylcellulose, and combinations thereof.

In some embodiments, the flavoring agent is selected from oil of peppermint, menthol, oil of spearmint, vanilla, oil of cinnamon, oil of wintergreen, lemon oil, orange oil, grape oil, lime oil, grapefruit oil, apple, apricot essence, clove oil, anise oil, cardamom oil, coriander oil, eucalyptus oil, fennel oil, lemongrass oil, nutmeg oil, and combinations thereof.

In some embodiments, the pharmaceutical active ingredient or pharmaceutical active is a food or nutraceutical bioactive agent. In some embodiments, the pharmaceutical active is selected from one or more of isoflavone, phytoestrogen, lycopene, anthocyanin, epigallocatechin gallate, resveratrol, psyllium seed husk, sulforaphane, isoflavone, flavonoid, antioxidant, or alpha-linolenic acid. In some embodiments, the pharmaceutical active comprises one or more cosmetic agents, veterinary medicine agents, functional ingredients, or combinations thereof.

In some embodiments, the pharmaceutical active composition further comprises about 0.1 to about 5 weight percent of a self-aggregating moiety, a self-assembling moiety, or both or a component thereof, based on the total weight of the composition. In some embodiments, the self-aggregating or self-assembling moieties are selected from one or more phospholipids, bile acids, bile salts, nanoplatelet structures, or edible clays. For example, calcium chloride can be used in combination with sodium alginate to create a self-assembling barrier gel. The ratio of pharmaceutical active to self-aggregating or self-assembling moieties can be about 100:1 to about 1:10 by weight.

In some embodiments, the pharmaceutical active composition pharmaceutical active composition further comprises about 0.1 to about 5 weight percent of an oxygen scavenger. In some embodiments, the oxygen scavenger is selected from one or more polyacids, polynucleic acids, proteins, polysaccharides, polypeptides, ethylenediamine tetra-acetic acid (EDTA) and salts thereof, glutamic acid and salts thereof, citric acid and salts thereof, phosphonates, histidine, phytochelatin, hemoglobin, chlorophyll, humic acid, transferrin, deferoxamine, vitamin E acetate, tocopherol, and combinations thereof. In some embodiments, the ratio of pharmaceutical active to oxygen scavenger is about 100:1 to about 1:10, 50:1 to about 1:5, or 20:1 to 1:1 by weight.

In some embodiments, the pharmaceutical active composition pharmaceutical active composition further comprises about 0.1 to about 5 weight percent a drug solubilizer.

In some embodiments, the delivery device is configured to provide directional delivery of the pharmaceutical active when placed in contact with the oral mucosa of a subject, such as a human.

In some embodiments, the polymer film is water erodible. In some embodiments, the polymer film is substantially devoid of the pharmaceutical active.

In some embodiments, the delivery device comprises one or more additional pharmaceutical active compositions, wherein said each of the additional pharmaceutical active compositions is substantially physically inseparable from the polymer film.

In some embodiments, the delivery device is configured such that the polymer film is placed in contact with the mucosa tissue of a subject when in use.

In some embodiments, a third layer comprises about 5-100 weight percent polymer matrix, based on the total weight of the layer.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

Figure 1A:
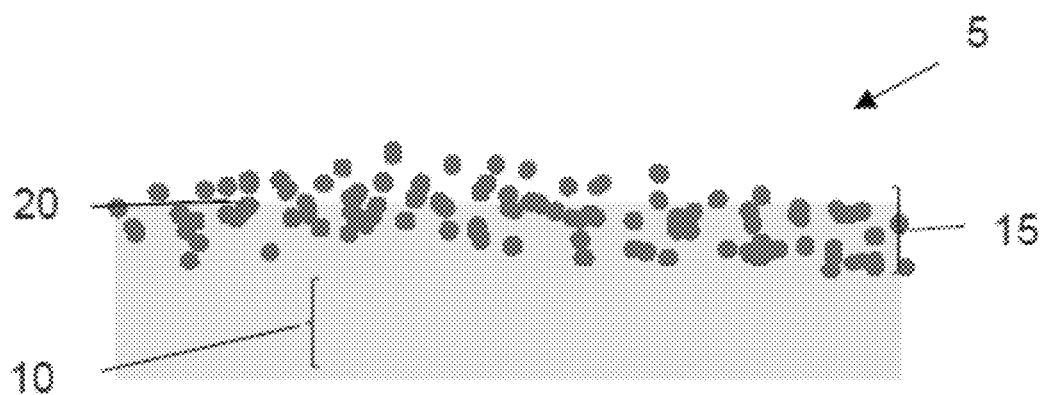
FIGS. 1a-1f are representations of transmucosal delivery devices comprising a polymer film and pharmaceutical active compositions.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a film" can include a plurality of such films, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Described herein is a pharmaceutical active-containing transmucosal delivery device comprising a polymer film and a pharmaceutical active composition disposed on a surface of the polymer film. The polymer film comprises a polymer matrix. The pharmaceutical active composition has a pH in a range of about 4 to about 9. The composition comprises at least one pharmaceutical active ingredient in the form of particles, wherein the particles have an average particle size of about 100 nm to about 5 microns. The composition further comprises an anti-crystallization agent and a pH adjusting agent, wherein the concentration of the pharmaceutical active ingredient is at least 20% w/w relative to the total weight of the pharmaceutical active composition. The drug composition pH can be different than a pH of the polymer matrix by greater than a 0.3 pH unit. The delivery device exhibits a residence time in the mouth of a subject ranging from about 5 minutes to about 30 minutes and is substantially mucoadhesive to a mucosa surface when placed sublingually under the tongue or placed buccally at the inner lining of the cheek.

The anti-crystallization agent may comprise various sugar alcohols and di-alcohols, including, for example one or more of sorbitol, mannitol, xylitol, isomalt, and the like. The anti-crystallization agent may be present in the composition in an amount that is about 10% to 40% w/w of the active ingredient. For example, the anti-crystallization agent may be present in the composition in an amount that is about 10%, 15%, 20%, 25%, 30%, 35%, or 40% w/w of the active ingredient. For example, if the weight of the active ingredient was 20 mg and the amount of anti-crystallization agent being used was 10 wt % of the active ingredient, the weight of the anti-crystallization agent in the composition would be 2 mg. The anti-crystallization agent may include a combination of one or more sugar alcohols, for example, a combination of sorbitol and mannitol. When sorbitol and mannitol are used collectively as the anti-crystallization agent, the amount of each may vary. For example, the ratio of the amount of sorbitol to mannitol may vary from 1-20:1 (sorbitol:mannitol). Thus, the ratio of sorbitol to mannitol may be 1:1, 5:1, 10:1, 15:1, and/or 20:1 or any ratio within the range of 1-20:1.

The pH adjusting agent may comprise a component selected from the group consisting of phosphate buffers, acetate buffers, citrate buffers, arginine buffers, TRIS buffers, histidine buffers, ammonium glycyrrhinate, and mixtures thereof.

The pharmaceutical active composition may further comprises one or more components selected from the group consisting of a fast dissolving polymer, a hydrogel polymer, a self-assembling or self-aggregating moiety, a dispersing agent, an oxygen scavenger, a drug solubilizing agent, a bioenhancer, a flavor agent, and a taste masking agent. The fast dissolving polymer may include a polymer that will dissolve in about 1 minute to about 3 minutes when placed in the mouth of a subject. The self-assembling or self-aggregating moiety may include one or more of phospholipids, bile acids, bile salts, nano-platelet structures, and edible clays. Moreover, divalent salts such as calcium, magnesium and zinc salts, in combination with hydrogels such sodium alginate and kappa carrageenan may be used to form a self-assembling barrier layer. It will be appreciated that the divalent salt may be present in the pharmaceutical active composition or it may be present in the polymer film. Correspondingly, the hydrogel may be present in the pharmaceutical active composition or it may be present in the polymer film. In embodiments, one of the hydrogel and the divalent salt is in the pharmaceutical active composition and the other of the hydrogel and the divalent salt is in the polymer film, such that when the divalent salt and the hydrogel come into contact with one another, they form a barrier layer. The self-assembling or self-aggregating moiety may also include hydrophobic self-assembling moieties.

In the delivery device, the pharmaceutical active ingredient is disposed in the form of particles directly on the surface of a relatively thin polymer film at concentrations of 20% weight active ingredient/weight active composition or higher. The delivery device can provide high active bioavailability and fast-onset-of-action while avoiding first pass metabolism. The average diameters of the active particles can range from less than 100 nanometers up to 5 micrometers in size.

In an embodiment, the delivery device comprises a composition of the pharmaceutical active ingredient wherein the pharmaceutical active ingredient resides at high concentrations (no less than 20% w/w) on the surface of an oral polymer film. The polymer film comprises a drug-free, dissolution rate-controlling, mucoadhesive polymer that offers residence time control from about 5 to about 30 min, provides effective taste masking of the pharmaceutical active ingredient, and adequate mucoadhesion when applied under the tongue (sublingual) or on to the inner lining of the cheek (buccal) inside a subject's mouth. The pharmaceutical active composition comprises nano- or microparticles of the pharmaceutical active ingredient, an anti-crystallization agent, a pH controlling buffer agent, a binding hydrogel polymer and a fast dissolving polymer.

The delivery device can provide enhanced permeation, rapid on-set of action, high active absorption, and reduced metabolites when applied under the tongue (sublingually) or on the inner lining of the check (buccally) in a subject's mouth.

The term "film" as used herein refers to a thin, flexible sheet of material and is intended to encompass coated films and film products. The term "pharmaceutical active" or "pharmaceutical active ingredient" as used herein refers to a substance or composition useful for the prevention and/or treatment of a condition in a subject. The term "subject" as used herein refers to an animal, including primates (monkey, ape, human, etc.) or non-primate (cow, horse, pig, cat, dog, rat, mouse, bird, fish, etc.).

FIG. 1a illustrates one embodiment of single layer delivery device 5 comprising a polymer film and a pharmaceutical active composition comprising a pharmaceutical active or salt thereof. Particularly, delivery device 5 comprises polymer film 10 comprising one or more polymer matrices and pharmaceutical active composition 15 comprising pharmaceutical active 20 (or a salt thereof). Importantly, pharmaceutical active composition 15 is not self-supporting and cannot physically be separated from the polymer film. In some embodiments, polymer film 10 is self-supporting. In some embodiments, the polymer film is positioned adjacent or directly adjacent to the pharmaceutical active composition. As used herein, the term "adjacent" refers to the positioning of two layers either in contact with each other directly or with another layer therebetween. The term "directly adjacent" refers to layers that are in contact with each other without any other layer therebetween.

Figure 1B:
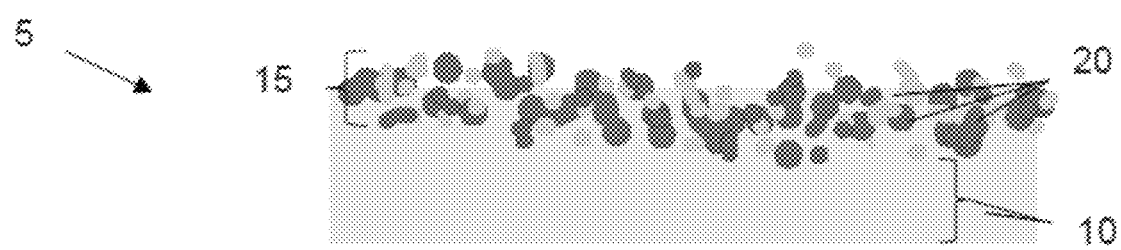
Figure 1C:
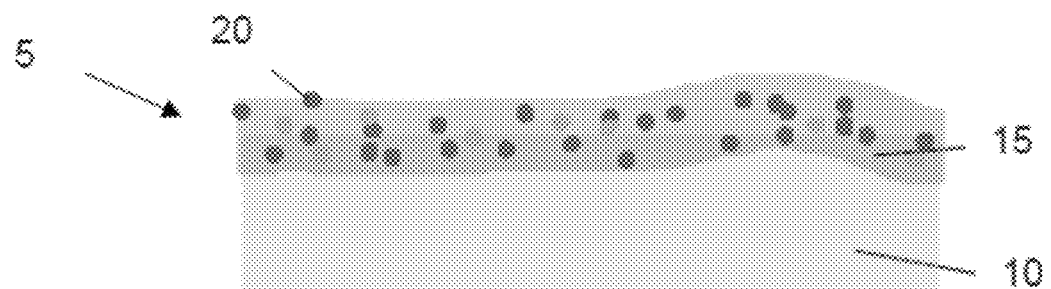
Figure 1D:
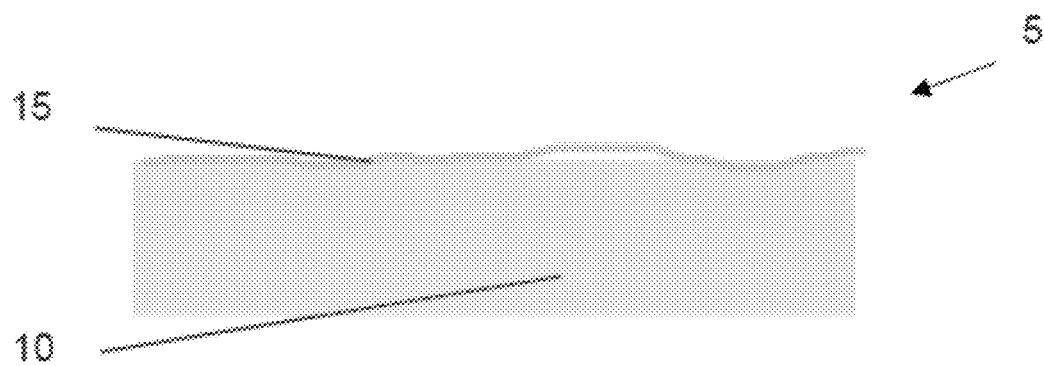

FIG. 1b illustrates an alternate embodiment of delivery device 5 wherein the pharmaceutical active composition is non-self-supporting and comprises a plurality of pharmaceutical actives 20. The term "non-self-supporting" describes a structure that cannot be physically separated to maintain mechanical integrity. Such domains can include (but are not limited to) extremely thin, fragile, discrete, and/or non-contiguous regions. FIGS. 1c and 1d illustrate alternate embodiments of delivery device 5 wherein pharmaceutical active 20 resides in pharmaceutical active composition 15 configured as a barrier matrix on a surface of the polymer film. As shown in FIG. 1d, pharmaceutical active composition 15 can be substantially thinner compared to polymer film 10, such as at least an order of magnitude thinner than the overall thickness of the film. For example, the thickness of polymer film 10 can be about 500%, 750%, 1000%, 2000%, 3000%, 4000%, 5000%, 7500% or 10000% of the thickness of pharmaceutical active composition 15. In some embodiments, the pharmaceutical active composition of delivery device 5 can be physically inseparable from the polymer film. Similarly, for example, the surface area of polymer film 10 can be about 100%, 150%, 200%, 250%, 300%, 350%, 400%, 450% or 500% of the surface area of pharmaceutical active composition 15. In some embodiments, the pharmaceutical active composition of delivery device 5 can be physically inseparable from the polymer filmpolymer film.

Figure 1E:
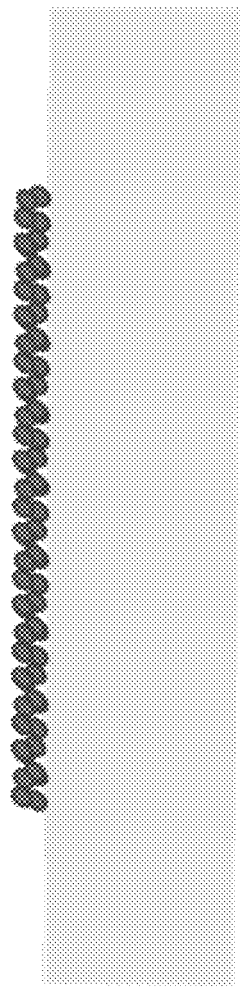
Figure 1F:
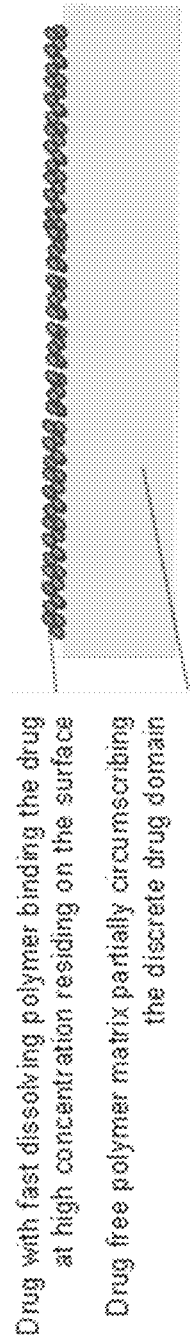

FIG. 1e and FIG. 1f illustrate additional alternative embodiments of the delivery device 5 wherein the pharmaceutical active composition has a relatively high concentration of pharmaceutical active ingredient. In FIG. 1e, the composition resides on the surface of the polymer film such that the polymer film is completely circumscribing the pharmaceutical active composition. That is, the pharmaceutical composition does not extend across the surface of the polymer film to edges thereof. In FIG. 1f, the pharmaceutical active composition comprises a fast dissolving polymer binding the composition to the surface of the polymer film. As in FIG. 1e, the composition resides on the surface of the polymer film such that the polymer film is completely circumscribing the pharmaceutical active composition. As set forth above, delivery device 5 is a single layer. The term "single layer" refers to a structure that does not include multiple layers that can easily be separated from each other, such as by peeling apart or wedging the regions away from each other. Thus, the disclosed delivery device includes a single layer with a polymer film having a pharmaceutical active composition disposed thereon, but is not a multi-layered, laminated structure. It should be appreciated that the polymer film 10 and the pharmaceutical active composition 15 can be discrete or contiguous in structure, unlike a layer that must be contiguous. In some embodiments, the delivery device comprises at least one component (i.e., polymer film or pharmaceutical active composition) with a thickness of no more than 500 μm in an unhydrated state. In some embodiments, each component in the delivery device 5 has a thickness of 500 μm or less.

Polymer film 10 comprises one or more polymer matrices and optionally one or more permeation enhancers, pH adjusting buffers or agents, taste masking agents, and/or flavors. Any desired polymer matrix can be used, including (but not limited to) water soluble, water swellable, and/or water erodible polymers. For example, in some embodiments, the polymer matrix can be selected from hydroxy propyl methyl cellulose (HPMC), methyl cellulose, hydroxyethyl cellulose (HPC), hydroxypropyl cellulose, polyvinyl pyrrolidone, sodium carboxymethyl cellulose, polyethylene oxide (PEO), pullulan, alginic acid, sodium alginate, polyethylene glycol, pectins, xanthan gum, tragancanth gum, guar gum, acacia gum, arabic gum, locust bean gum, gellan gum and combinations thereof, polyacrylic acid, POLYCARBOPHIL®, methyl methacrylate copolymer, carboxy vinyl copolymers, natural and hydrolyzed starch, gelatin type A and B, carrageenan, and combinations thereof.

As used herein the phrase "water soluble polymer" and variants thereof refer to a polymer that is at least partially soluble in water, fully or predominantly soluble in water, or absorbs water. Polymers that absorb water are often referred to as being water swellable polymers. In some embodiments, materials used in the polymer matrix of polymer film 10 can be water soluble or water swellable at room temperature and/or other temperatures, such as temperatures exceeding room temperature.

In some embodiments, the polymer matrix can be present in an amount of about 5-100 weight percent of the total weight of the polymer film (e.g., about 5, 10, 15, 20, 25, 30, 35, 40, 45, 50, 55, 60, 65, 70, 75, 80, 85, 90, 95, or 100 weight percent, based on the total weight of the domain). The polymer matrix provides a self-supporting structure and desired residence time for improved bioavailability.

Polymer film 10 can optionally include any known permeation enhancer known or used in the art. The term "permeation enhancer" refers to a component used to enhance the penetration rate of a pharmaceutical active through the skin. Suitable permeation enhancers can include (but are not limited to) lipophilic solvents, surfactants, menthol, fatty acid esters and derivatives, polyhydric alcohols, bile salts, chelators, cyclodextrins and chitosan and combinations thereof. For example, suitable permeation enhancers can include (but are not limited to) chitobiose, chitosan, imethyl sulfoxide (DMSO), linoleic acid (LA), isopropyl myristate (IPM), sodium glycodeoxycholate (GDC), beta-cyclodextrin, oleic acid (OA), and combinations thereof. In some embodiments, the permeation enhancer can be present in an amount of about 0-5 weight percent of the total weight of the polymer film (e.g., 0, 0.5, 1, 1.5, 2, 2.5, 3, 3.5, 4, 4.5, or 5 weight percent).

Polymer film 10 can further include one or more pH-adjusting buffers. Any buffer that can resist a change in pH can be used. For example, in some embodiments, the buffer can be selected from phosphate, acetate, citrate, arginine, TRIS, and histidine buffers. For example, in some embodiments a citric acid buffer can be used. In some embodiments, the buffer can be present in an amount of about 0-5 weight percent of the total weight of the polymer film (e.g., 0, 0.5, 1, 1.5, 2, 2.5, 3, 3.5, 4, 4.5, or 5 weight percent).

The polymer film can optionally include taste masking agents and/or flavoring agents to improve the flavor of the film. The term "taste masking agent" refers to an agent that is added to a composition to mask the taste of one or more unpleasant tasting components. The term "flavoring agent" refers to any additive that gives the disclosed film a desired taste or smell. Suitable taste masking agents can include (but are not limited to) cellulose acetate, cellulose acetate butyrate, ethylcellulose, methylcellulose, and combinations thereof. Suitable flavoring agents can include (but are not limited to) natural and artificial flavors such as oil of peppermint, menthol, oil of spearmint, vanilla, oil of cinnamon, oil of wintergreen, lemon oil, orange oil, grape oil, lime oil, grapefruit oil, apple flavor oil, raspberry oil, strawberry oil, pear oil, blueberry oil, blackberry oil, watermelon flavor, cherry oil, licorice oil, apricot essence, clove oil, anise oil, cardamom oil, coriander oil, eucalyptus oil, fennel oil, lemongrass oil, nutmeg oil, and combinations thereof. In some embodiments, the taste masking agents and/or flavoring agents can be present in an amount of about 0-5 weight percent of the total weight of the polymer film (e.g., 0, 0.5, 1, 1.5, 2, 2.5, 3, 3.5, 4, 4.5, or 5 weight percent).

In some embodiments, the local pH of the polymer film is about 3.5 to about 8.5, such as about 3.5, 4, 4.5, 5, 5.5, 6, 6.5, 7, 7.5, 8, or 8.5. In some embodiments, the local pH of the pharmaceutical active composition is between 4 and 9, such as between 5 and 8, or between 6 and 7. In some embodiments, the pH of delivery device 5 is between 3 and 9, such as between 4.5 and 7.5 or between 5 and 7.

Pharmaceutical active composition 15 comprises at least one pharmaceutical active 20 or a salt thereof. In some embodiments, pharmaceutical active 20 can be an ace inhibitor (such as Benazepril, Captopril, Enalapril, Lisinopril, Moxepril, Perindopril, Quinapril, Ramipril and/or Trandolapril), addiction medicine (such as buprenorphine, disulfiram, nalmefene, naltrexone, cannabidiol, nalfurafine, naltrexone, and/or varenicline), alpha-1 adrenergic blockers (such as alfuzosin, doxazosin, prazosin, tamsulosin and/or terazosin), ALS agents (such as riluzole), Alzheimer's disease medications (such as donepezil, galantamine, rivastigmine, and/or memantine), allergy, antipyretic and antibiotics medications (such as allopurinol, azelastine, beclomethasone, budesonide, desmopres sin, fluticasone, phenylephrine, barbiturates, metronidazole, carbamazepine, cimetidine, ibuprofen, penicillins, amoxicillin, cloxacillin, dicloxacillin, ticarcillin, phenyloin, quinidine, streptomycin and/or vancomycin), analgesics and anesthetics (such as ketamine, pentozocine, propofol, fentanyl, buprenorphine, oxycodone, hydrocodone, and/or nalbuphine); amlexanox, benzocaine, carbamide, peroxide, nystatin, lidocaine, and/or pilocarpine), angiotensin II receptor blockers (such as candesartan, eprosartan mesylate, olmesartan, telmisartan, and/or valsartan), anti-arrhythmics (such as adenosine, amiodarone, atropine, epinephrine, mexiletine, moricizine, procainamide, propafenone, quinidine, sotalol, and/or verapamil), antispasmotic and anticholinergics (such as hyoscyamine, scopolamine, darifenacin, oxybutynin, solifenacin, tolterodine, glycopyrrolate, hyoscyamine, oxybutynin, propantheline, scopolamine, promethazine, flavoxate, trospium, and/or tolterodine), anticonvulsants (such as carbamazepine, clonazepam, diazepam, ethosuximide, felbamate, pregabalin, levetiracetam, lamotrigine, lorazepam, midazolam, oxcarbazepine, phenobarbital, tiagabine, topiramate, and/or valproic acid), antidepressants (such as asenapine, buproprion, buprenorphine, citalopram, desipramine, doxepin, duloxetine, escitalopram, fluoxetine, fluvoxamine, imipramine, mirtazapine, nefazodone, nortriptyline, nortriptyline, sertraline, trazodone, and/or venlafaxine), anti-diarrheals (such as diphenoxylate, atropine, loparimide, and/or bismuth subsalicylate), anti-diabetic agents (such as acarbose, miglitol, and metformin, AVANDAMET®, glucovance, metaglip, metaglip, rosiglitazone, osiglitazone, repaglinide, chlorpropamide, glimepiride, glyburide, glipizide, tolazamide, tolbutamide, glucagon, extenatide, and/or pramlintide), antibodies and immunological drugs (such as adalimumab, anakinra, alitretinoin, becaplermin, calamine, doxepin, fluorouracil, masoprocol, pimecrolimus, tacrolimus, auranofin, azathioprine, etanercept, hydroxychloroquine, infliximab, leflunomide, methotrexate, and/or sulfasalazine), anti-emetics (such as aprepitant, dolasetron, droperidol, granisetron, metoclopramide, ondansetron, prochlorperazine, scopolamine, promethazine, and/or trimethobenzamide), antifungals (such as amphotericin B, anidulafungin, caspofungin, clotrimazole fluconazole, flucytosine, griseofulvin, itraconazole, ketoconazole, micafungin, nystatin, posaconazole, terbinafine, voriconazole, butenafine, ciclopirox, clotrimazole, enconazole, ketoconazole, miconazole, naftifine, nystatin, oxiconazole terbinafine, butenafine, ciclopirox, clotrimazole, econazole, ketoconazole, miconazole, naftifine, nystatin, oxiconazole, terbinafine clindamycin, metronidazole, butoconazole, clotrimazole, miconazole, terconazole and tioconazole, and/or tolnaftate), anti-hepatitis (such as adefovir, entecavir, lamivudine, peginterferon alfa-2a, peginterferon alfa-2b, rebetron, and/or ribavirin), anti-herpetic agents (such as acyclovir, famciclovir, valacyclovir, acyclovir, docosanol, and/or penciclovir), antihistamines (such as cetirizine, desloratadine, fexofenadine, loratadine, chlorpheniramine, clemastine, cyproheptadine, dimenhydrinate, diphenhydramine, and/or hydroxyzine), anti-hypertension (such as benazepril, captopril, enalapril, lisinopril, moexipril, losartan, valsartan, atenolol & chlorthalidone, bisoprolol, metoprolol, nadolol & bendroflumethazide, propranolol, timolol, amlodipine & benazepril, verapamil & trandolapril, amiloride, spironolactone, triamterene, clonidine, hydralazine, methyl-dopa, and/or prazosin & polythiazide), antihypertensives (such as aliskiren, aliskiren, epoprostenol, fenoldopam, hydralazine, minoxidil, nitroprusside, phentolamine, and/or treprostinil), anti-influenza agents (such as oseltamivir phosphate, rimantadine and/or zanamivir), anti-malarials, anti-protozoals, amebicides (such as atovaquone, chloroquine, Iodoquinol, mefloquine, primaquine, pyrimethamine, pyrimethamine, pyruvium, sulfadoxine, and/or quinine), anti-platelet agents (such as abciximab, dipyridamole/ASA, anagrelide, cilostazol, clopidogrel, dipyridamole, eptifabatide, ticlopidine, and/or tirofiban), antipsychotics (such as aripiprazole, chlorpromazine, clozapine, fluphenazine, haloperidol, loxapine, molindone, amantadine, rimantadine, and memantine, olanzepine, perphenazine, pimozide, quetiapine, risperidone, thioridazine, thiothixine, trifluoperazine, ziprasidone, and/or lithium), antispasmotics (such as dicyclomine, donnatal extentabs, propantheline, simethicone, hyoscyamine, LIBRAX®, tegaserod, baclofen, carisprodol, cyclobenzaprine, cyclobenzaprine, diazepam, metaxalone, orphenadrine, and/or bellergalS), anti-herpetic agents (such as acyclovir, famciclovir, valacyclovir, docosanol, and/or penciclovir), antihypertensives (such as captopril, clonidine, enalaprilat, esmolol, fenoldopam mesylate, hydralazine, labetalol, nicardipine, and/or nitroglycerin), anti-tussives/expectorants (such as benzonatate and/or guaifenesin), atopic dermatitis medications (such as pimecrolimus and/or tacrolimus), antianxiolytic agents (such as benzodiazepines and non-benzodiazepine sedatives like alprazolam, buspirone, chlordiazepoxide, chlorazepate, clonazepam, diazepam, estazolam, eszcpiclone, flurazepam, lorazepam, midazolam, oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol, and/or timolol), bile acid sequestrants (such as cholestyramine, colesevelam, and/or colestipol), bisphosphonates (such as alendronate, etidronate, pamidronate, risedronate, tiludronate and zoledronic acid, raloxifene, and/or teriparatide), benign prostatic hypertrophy medications (such as alfuzosin, doxazosin, dutasteride, finasteride, tamsulosin, and/or terazosin), calcium channel blockers (such as amlodipine, bepridil, diltiazem, felodipine, isradipine, nicardipine, nifedipine, and/or nisoldipine), cephalosporins (such as cefadroxil, cefazolin, cephradine, cephalexin, cefaclor, cefotetan, cefoxitin, cefprozil, cefuroxime, cefuroxime, loracarbef, cefdinir, cefixime, cefoperazone, cefotaxime, cefpodoxime, ceftazidime, ceftibuten, ceftizoxime, and/or cefepime), colony stimulating factors (such as darbepoietin alfa, erythropoietin, filgrastim, oprelvekin, pegfilgrastim, and/or sargramostim), corticosteroids (such as budesonide, cortisone acetate, dexamethasone, fludrocortisones, hydrocortisone, methylprednisolone and prednisone, MEDROL®, aclometasone dipropionate, desonide, flucinolone acetonide, Hydrocortisone, betamethasone dipropionate, betamethasone valerate, clocortolone pivalate, desoximetasone, fluocinolone acetonide, flurandrenolide, fluticasone propionate, chydrocortisone butyrate, hydrocortisone valerate, mometasone furoate, prednicarbate, triamcinolone, amcinonide, augmented Betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate, and/or triamcinolone acetonide), decongestants (such as phenylephrine and/or pseudoephedrine), diuretics (such as acetazolamide, amiloride, amiloride and HCTZ 4endroflumethiazide, bumetanide, chlorothiazide, chlorthalidone, dichlorphenamide, eplenerone, ethacrynic acid, furosemide, hydrochlorothiazide, HCTZ/triampterene, hydroflumethiazide, indapamide, methazolamide, methyclothiazide, methyclothiazide, metolazone, polythiazide, spironolactone, spironolactone, HCTZ torsemide, trichlormethiazide, and/or triamterene), endocrine agents (such as bromoc cinacalcet cosyntropin, riptine, cabergoline, calcitonin, desmopressin, Leuprolide, octreotide, and/or vasopressin), erectile dysfunction agents (such as sildenafil, tadalafil, and/or vardenafil), fibrates (such as clofibrate, fenofibrate, and/or gemfibrozil), fluoroquinolones (such as ciprofloxacin, gatifloxacin, levofloxacin, moxifloxacin, norfloxacin, and/or ofloxacin), gastrointestinal agents (such as alosetron, infliximab, mesalamine, misoprostol, neomycin, octreotidev, osalazine, orlistat, sucralafate, vasopressinallopurinol, colchicine, probenecid, cimetidine, famotidine, nizatidine, ranitidine, balsalazide, budesonide, infliximab, mesalamine, olsalazine, and/or sulfasalazine), Interferon (such as Interferon alfa-2A, Interferon alfa-2b, Interferon alfa-2b and ribavirin combo pack, Interferon alfa-N3, Interferon beta-1A, Interferon beta-1B (BETASERON®), cilostazol, and/or pentoxifylline), immunizations (such as Comvax, diphtheria-tetanus toxoid, hepatitis A vaccine, hepatitis B vaccine, influenza vaccine, Fluzone, lyme disease vaccine, and/or PNEUMOVAX® 23), heparins (such as dalteparin, danaparoid, enoxaparin, tinzaparin, and/or fondaparinux) macrolides (such as azithromycin, clarithromycin, and/or erythromycin), migraine medication (such as almotriptan, eletriptan, frovatriptan, naratriptan, rizatriptan, sumatriptan, zolmitriptan, and/or dihydroergotamine), neuromuscular blockers (such as atracurium, cisatracurium, doxacurium, mivacurium, pancuronium, rocuronium, succinylcholine, vecuronium, mivacurium, rapacuronium, rocuronium, succinylcholine, atracurium, cisatracurium, pancuronium, vecuronium, doxacurium, pipecuronium, and/or tubocurarine), nitrates (such as isosorbide dinitrate, isosorbide mononitrate, and/or nitroglycerin), NSAIDs (such as arthrotec, diclofenac, etodolac, indomethacin, ketorolac, sulindac, tolmentin, diflunisal salsalate meloxicam, piroxicam, nabumetone flurbiprofen, ibuprofen, ketoprofen, naproxen, oxaprozin, celecoxib, rofecoxib, and/or valdecoxib), opiates (such as codeine, fentanyl, hydrocodone, hydromorphone, meperidine methadone, morphine, oxycodone, propoxyphene, tramadol, paracetomol, buprenorphine, butorphanol, nalbuphine, pentazocine, nalmefene, naloxone, ziconotide meperidine, and/or morphine), Parkinson's disease treatments (such as amantadine, benztropine, bromocriptine, entacapone, pergolide, pramipexole, ropinirole, selegiline, SINEMET®, tolcapone, and/or trihexyphenidyl), proton pump inhibitors (such as esomeprazole, lansoprazole, omeprazole, pantoprazole, and/or rabeprazole sodium), psoriasis medications (such as acitretin, alefacept, anthralin, calcipotriene, efalizumab, and/or tazarotene), pulmonary medications (such as ipratropium, tiotropium, albuterol, bitolterol, levalbuterol, pirbuterol, metaproterenol, formoterol, salmeterol, ADVAIR®, SYMBICORT®, beclomethasone, budesonide, flunisolide, fluticasone, Mometasone furoate, triamcinolone, montelukast, zafirlukast, cromolyn sodium, nedocromil, acetylcysteine, and/or aminophylline/theophylline), HMG COA reductase inhibitors (such as atorvastatin, fluvastatin, lovastatin, pravastatin, rosuvastatin, simvastatin, and/or ezetimibe), stimulants (such as atomoxetine, benzphetamine, caffeine, dexmethylphenidate, dextroamphetamine, diethylpropion, methylphenidate, modafinil, pemoline, phendimetrizine, phentermine and sibutramine), tetracycline (such as doxycycline, minocycline, and/or tetracycline), urology medication (such as pentosan, bethanecol, and/or phenazopyridine), vasodilators and vasopressors (such as fenoldopam mesylate, hydralazine, nesiritide, nitroglycerin, dobutamine, dopamine, epinephrine, inaminone, milrinone, nicotine, norepinephrine, phenylephrine, and/or vasopressin).

In some embodiments, the pharmaceutical active can be a food or nutraceutical bioactive agent selected from one or more constituents in foods and/or dietary supplements that are responsible for changes in health status. For example, the pharmaceutical active can include (but is not limited to) components of plants, such as fruits and vegetables, e.g., isoflavones and phytoestrogens found in soy, lycopene found in tomatoes, flavonoids such as anthocyanins found in berries, epigallocatechin gallate (EGCG) found in green tea, resveratrol found in red grape products, soluble dietary fiber products such as psyllium seed husk, sulforaphane from broccoli, isoflavanoids from soy or clover, flavonoids, antioxidants, alpha-linolenic acid from flax seeds, extracts such as ginseng, garlic oil, etc.

In some embodiments, the pharmaceutical active can be a biological active (e.g., a biologically active substance in plants that has proven beneficial effects on health (such as the cholesterol-lowering effects of phytosterols) and/or potential beneficial effects on health (such as phytochemicals and/or phytonutrients)). For example, suitable biological actives can include (but are not limited to) phytochemicals in leaves, stems, roots, tubers, buds, fruits, seeds and flowers, and plant-derived foods and drinks (such as tea, coffee, alcoholic beverages). Suitable biological actives can further include flavonoids found in a range of plant-derived foods, including tea, wine, onions, apples and berries; phenolic acids found in tea and coffee; and/or carotenoids (some of which are precursors of vitamin A) prevalent in red, green, and orange fruits and vegetables.

Pharmaceutical active 20 can further include one or more cosmetic agents, veterinary medicine agents, functional ingredients, and the like. Examples include alpha linoleic acid (ALA), cannabidiols (CBD), coenzyme Q10, curcumin, chondroitin, glucosamine, glutamine, hemp oils, lutein, L-Carnitine, melatonin, methionine, neem, omega-3 and -6 fish oil, St. John's Wort, saw palmetto, ubiquinone, vitamins, xylitol, or zeazanthin.

Pharmaceutical active 20 can be a solid solution, amorphous, and/or in a monomorphic crystalline microparticle state. For example, the pharmaceutical active can be present as solid solution or a substantially-uniform, dispersed, amorphous microparticle residing on the surface of the first discrete domain. The term "solid solution" as used herein refers to a solid that is molecularly dispersed in a domain to form a glassy state. The term "amorphous" as used herein refers to a solid material with molecular structures that do not have a definite geometric shape or a lattice pattern as assessed by XRT diffraction. Amorphous particles can have a glass point, a gel point, and can lack a crystalline lattice structure. In embodiments, amorphous particles are preferred for increasing bioavailability of the pharmaceutical active ingredient. "Monomorphic crystalline state" refers to a crystal state of one lattice configuration. In embodiments, the term "microparticle" as used herein refers to a particle with a diameter of about 0.001-100 μm. In some embodiments, suitable amorphous microparticles have a diameter of less than about 25 μm, 10 μm, 5 μm, 1 μm, 0.5 μm or 0.1 μm.

In some embodiments, the pharmaceutical active composition 15 can comprise one or more self-aggregating and/or self-assembling moieties that provide permeation enhancement characteristics. The term "self-assembling" as used herein refers to molecular structures that arrange themselves upon induced physical change and/or triggered phase transition to minimize the overall free energy of the system, resulting in a thermodynamically stable system. The term "self-aggregating" refers to a structure resulting from the ability of a molecule to aggregate into high concentration domains or "rich domains." In some embodiments, the self-aggregating and/or self-assembling moieties can be present in an amount of about 0-5 weight percent of the total weight of the pharmaceutical active composition (e.g., 0, 0.5, 1, 1.5, 2, 2.5, 3, 3.5, 4, 4.5, or 5 weight percent). The self-aggregating and/or self-assembling moieties provide directional permeation.

In some embodiments, suitable self-aggregating and/or self-assembling moieties can include (but are not limited to) phospholipids, bile salts, nanoplatelets, clays, polar lipids, or combinations thereof. For example, calcium chloride can be used in combination with sodium alginate to create a self-assembling barrier gel. It will be appreciated that calcium chloride may be present in the pharmaceutical active composition or it may be present in the polymer film. Correspondingly, the sodium alginate may be present in the pharmaceutical active composition or it may be present in the polymer film. In embodiments, one of the sodium alginate and the calcium chloride is in the pharmaceutical active composition and the other of the sodium alginate and the calcium chloride is in the polymer film, such that when they come into contact with one another, they form a barrier layer. Additionally, suitable examples of the self-aggregating and/or self-assembling moieties can include phosphatidylcholine, phosphatidic acid, phosphatidylcholine, phosphatidylethanolamine, phosphatidylglycerol, phosphatidylcholine, phosphatidylserine, phosphatidylinositol, phosphatidylinositol phosphate, phosphatidylinositol bisphosphate, phosphatidylinositol triphosphate, and/or sphingomyelin. More specifically, the self-aggregating and/or self-assembling moieties can comprise 1,2-didecanoyl-sn-glycero-3-phosphocholine, 1,2-dierucoyl-sn-glycero-3-phosphate (sodium salt), 1,2-dierucoyl-sn-glycero-3-phosphocholine, 1,2-dierucoyl-sn-glycero-3-phosphoethanolamine, 1,2-dierucoyl-sn-glycero-3[phospho-rac-(1-glycerol . . . ) (sodium salt), 1,2-dilinoleoyl-sn-glycero-3-phosphocholine, 1,2-dilauroyl-sn-glycero-3-phosphate (sodium salt), 1,2-dilauroyl-sn-glycero-3-phosphocholine, 1,2-dilauroyl-sn-glycero-3-phosphoethanolamine, 1,2-dilauroyl-sn-glycero-3[pPhospho-rac-(1-glycerol) (sodium salt), 1,2-dilauroyl-sn-glycero-3 [phospho-rac-(1-glycerol) (ammonium aalt), 1,2-dilauroyl-sn-glycero-3-phosphoserine (sodium salt), 1,2-dimyristoyl-sn-glycero-3-phosphate (sodium salt), 1,2-dimyristoyl-sn-glycero-3-phosphocholine, 1,2-dimyristoyl-sn-glycero-3-phosphoethanolamine, 1,2-dimyristoyl-sn-glycero-3 [phospho-rac-(1 glycerol . . . ) (sodium salt), 1,2-dimyristoyl-sn-glycero-3[phospho-rac-(1-glycerol . . . ) (ammonium salt), 1,2-dimyristoyl-sn-glycero-3[phospho-rac-(1-glycerol . . . ) (sodium/ammonium salt), 1,2-dimyristoyl-sn-glycero-3-phosphoserine (sodium salt), 1,2-dioleoyl-sn-glycero-3-phosphate (sodium salt), 1,2-dioleoyl-sn-glycero-3-phosphocholine, 1,2-dioleoyl-sn-glycero-3-phosphoethanolamine, 1,2-dioleoyl-sn-glycero-3[phospho-rac-(1-glycerol . . . ) (sodium salt), 1,2-dioleoyl-sn-glycero-3-phosphoserine (sodium salt), 1,2-dipalmitoyl-sn-glycero-3-phosphate (sodium salt), 1,2-dipalmitoyl-sn-glycero-3-phosphocholine, 1,2-dipalmitoyl-sn-glycero-3-phosphoethanolamine, 1,2-dipalmitoyl-sn-glycero-3 [phospho-rac-(1-glycerol.) (sodium salt), 1,2-dipalmitoyl-sn-glycero-3[phospho-rac-(1-glycerol) (ammonium salt), 1,2-dipalmitoyl-sn-glycero-3-phosphoserine (sodium salt), 1,2-distearoyl-sn-glycero-3-phosphate (sodium salt), 1,2-distearoyl-sn-glycero-3-phosphocholine, 1,2-distearoyl-sn-glycero-3-phosphoethanolamine, 1,2-distearoyl-sn-glycero-3[phospho-rac-(1-glycerol . . . ) (sodium salt), 1,2-distearoyl-sn-glycero-3[phospho-rac-(1-glycerol) ammonium salt), 1,2-distearoyl-sn-glycero-3-phosphoserine (sodium salt), hydrogenated egg PC hydrogenated soy PC, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-oleoyl-sn-glycero-3 [phospho-rac-(1-glycerol)] (sodium salt), 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine, 1-stearoyl-2-palmitoyl-sn-glycero-3-phosphocholine, 1-stearoyl-2-palmitoyl-sn-glycero-3-phosphocholine; edible clay components such as sodium bentonite, polyphosphate, montmorillonite, kaolin, cloisite; bile acids and salts that include cholic acid, sodium and calcium cholates salts, chenodeoxycholic acid, sodium and calcium chenodeoxycholates salts, chenodeoxycholic acid, sodium and calcium chenodeoxycholates salts, glycocholic acid, sodium and calcium glycocholates salts, glycyrrhetinic acid, glycyrrhentinate sodium, taurocholic acid, sodium and calcium taurocholates salts, lithocholic acid, sodium and calcium lithocholates salts; nanoplatelets, bentonite, cloisite, and/or combinations thereof.

In some embodiments, pharmaceutical active composition 15 can optionally comprise one or more oxygen scavengers. The term "oxygen scavenger" as used herein refers to a composition that reduces or eliminates the generation of unwanted oxidation products. In some embodiments, the oxygen scavenger is effective to absorb oxygen. Suitable oxygen scavengers that can be incorporated into pharmaceutical active composition 15 can include (but are not limited to) ascorbates, isoascorbates, tannins, sulfites, oxidizable polymers, polyacids, polynucleic acids, proteins, polysaccharides, polypeptides, ethylenediamine tetraacetic acid (EDTA) and salts thereof, organic glutamic acid and salts thereof, citric acid and salts thereof, phosphonates, histidine, phytochelatin, hemoglobin, chlorophyll, humic acid, transferrin, desferrioxamine, vitamin E acetate, tocopherol, and combinations thereof. In some embodiments, the oxygen scavenger can be present in an amount of about 0-5 weight percent of the total weight of the pharmaceutical active composition (e.g., 0, 0.5, 1, 1.5, 2, 2.5, 3, 3.5, 4, 4.5, or 5 weight percent).

In some embodiments, the ratio of pharmaceutical active to oxygen scavenger is about 100:1 to about 1:10, such as about 100:1, 90:1, 80:1, 70:1, 60:1, 50:1, 40:1, 30:1, 20:1, 10:1, 1:1, 1:2, 1:3, 1:4, 1:5, 1:6, 1:7, 1:8, 1:9, or 1:10. It should be appreciated that the oxygen scavenger can improve the oxidative stability of the pharmaceutical active or a pharmaceutically acceptable salt thereof. The oxygen scavenger can further improve the oxidative stability of one or more self-aggregating and/or self-assembling moieties when present in the disclosed film or layer.

In some embodiments, pharmaceutical active composition 15 can optionally comprise one or more drug solubilizers. The term "drug solubilizer" as used herein refers to an agent that forms a solubilized phase of a pharmaceutical active. Suitable drug solubilizers can include (but are not limited to) solvents, oils, surfactant, or phospholipids. In some embodiments, the drug solubilizer can be present in an amount of about 0-5 weight percent of the total weight of the pharmaceutical active composition (e.g., 0, 0.5, 1, 1.5, 2, 2.5, 3, 3.5, 4, 4.5, or 5 weight percent).

In some embodiments, delivery device 5 can include more than a polymer film and a pharmaceutical active composition. For example, the disclosed device can include a polymer film comprising a film-forming polymeric matrix and optionally one or more pH adjusting buffer, taste masking agent, and/or flavor to provide effective taste masking and/or directional permeation. The device can include a second polymer film comprising a self-assembling phospholipid and/or bile salts to provide permeation enhancement. The device can further comprise a pharmaceutical active composition that includes at least one pharmaceutical active or its salts thereof and optionally a mucoadhesive polymer, pH adjusting buffer, and/or oxygen scavenger to provide mucoadhesion and/or a high driving force resulting from a high concentration microenvironment when placed in contact with the oral mucosa.

In some embodiments, delivery device 5 can be a mucoadhesive film. The term "mucoadhesive" as used herein refers to the attachment of synthetic or natural polymers to a biological substrate, as defined by Robinson, J R, "Rationale of Bioadhesion/mucoadhesion", in Gurny R., Junginger, H. E. eds. Bioadhesion: Possibilities and Future Trends, Stuttgart: Wissenschaftliche Verlagsesellschaft, Stuttgart, pages Vol. 13 page 15 (1990), the entire content of which is incorporated by reference herein. There is currently no known single-layer delivery device that comprises a polymer film and a pharmaceutical active composition disposed thereon, wherein the pharmaceutical active composition is rich in pharmaceutical active, and at least one of the pharmaceutical active composition or the polymer film provides effective taste masking and enhanced transmucosal absorption when the pharmaceutical active composition is placed in contact with the oral mucosa. In some embodiments, at least one of the pharmaceutical active composition or the polymer film provides enhanced transmucosal absorption. In some embodiments, the mucoadhesive polymer provides enhanced absorption when the polymer film is placed in contact with the mucosa tissue of a subject.

Figure 2:
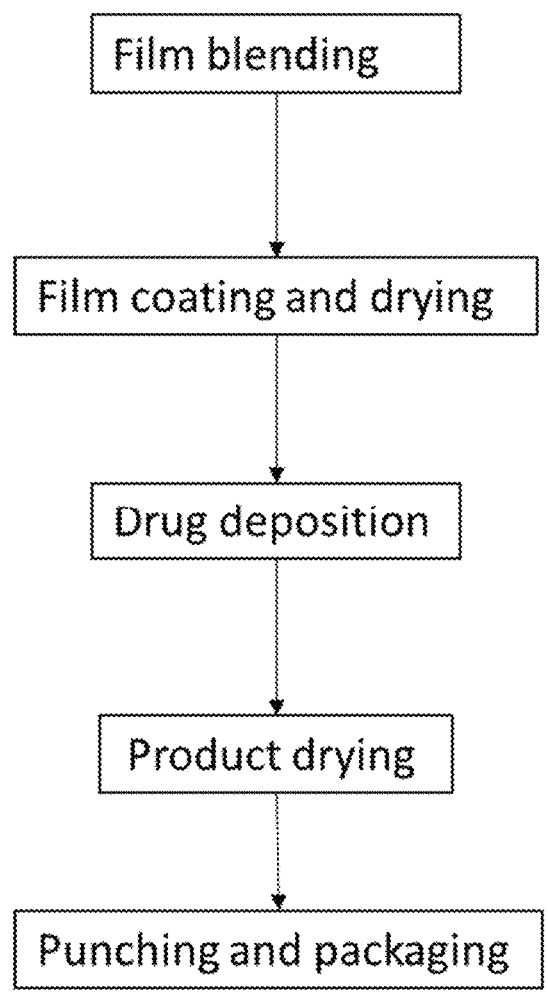
FIG. 2 is a schematic representation of an exemplary process flow diagram for the manufacturing process.

In embodiments, a method of manufacturing the pharmaceutical active-containing transmucosal delivery device comprises blending a polymer matrix and a pH adjusting agent; solubilizing the blend; casting the blend into a wet polymer film; drying the polymer film; applying a pharmaceutical active composition onto a surface of the polymer film, wherein a viscosity of the composition is from about 1 cP to about 100 cP; and heating the polymer film with the pharmaceutical active composition applied thereto in order to form the pharmaceutical active-containing transmucosal delivery device. FIG. 2 provides an exemplary schematic process flow diagram of the manufacturing process.

In embodiments, the method of manufacture may include a method of forming a continuous and uniform single layer active delivery device comprising domain polymer film and a pharmaceutical active composition, wherein the polymer film and the composition are substantially inseparable. For example, a delivery device can be constructed by preparing a polymer film comprising a wet polymer matrix and one of more of a permeation enhancer, pH adjusting buffer, taste masking agent, and/or flavor agent using a first solvent. A wet polymer film is formed by casting the wet polymer matrix. A drying apparatus can be used to dry the wet polymer matrix and expose the wet polymer film to a temperature sufficient to flash off the first solvent and thereby dry the polymer film as a continuous single layer film laminate. A second wet solution or suspension comprising a pharmaceutical active can then be prepared using a second solvent. A predetermined amount of the second wet solution is applied via spraying, electro-spraying, atomized coating, and/or ultra-thin web-coating processes onto selected areas on a surface of the first dry polymer film. The film with the pharmaceutical active composition applied thereto is then dried in a drying apparatus and exposed to a temperature sufficient to flash off the second solvent to form a pharmaceutical active-containing delivery device. In some embodiments, the heating and drying temperature can range from about room temperature to about 250° C.

In embodiments where delivery device 5 is a transmucosal single layer film device, the film delivery device be prepared by procuring a dry, drug-free web-coated polymer matrix laminate roll from a suitable vendor (such as Lohmann Therapie Systeme (LTS), Tapemark Inc, Aquestive Therapeutics, or ARx LLC). The second wet solution or suspension comprising a pharmaceutical active can then be prepared using a second solvent. A predetermined amount of the second wet solution or suspension can be applied onto selected areas of the surface of the dry polymer film by spraying, electro-spraying, atomized coating, and/or ultra-thin web-coating processes. The wet film with the pharmaceutical active composition applied thereto can then be deposited in a drying apparatus and exposed to a heating temperature sufficient to flash off the second solvent (e.g., about room temp to 250° C.) to form a pharmaceutical active-containing delivery device. In some embodiments, the pharmaceutical active composition comprising the pharmaceutical active is substantially thinner than the polymer film.

In some embodiments, transmucosal single layer delivery device 5 can be constructed by preparing a first wet polymer matrix and one or more of a permeation enhancer, pH adjusting buffer, taste masking agent, and/or a flavor using a first solvent. A first wet film can be formed by casting the wet polymer matrix. A second wet solution or suspension comprising pharmaceutical active 20 (or a salt thereof) and an oxygen scavenger and/or a drug solubilizer can be prepared in a second solvent. A predetermined amount of the second wet solution or suspension can then be applied on a surface of the first wet polymer film to form a wet multi-domain film using spraying, electro-spraying, atomized coating, and/or ultra-thin web-coating processes. The wet multi-domain film can be deposited in a drying apparatus and exposed to a heating temperature sufficient to flash off the first and second solvents (e.g., about room temp to 250° C.) to form a delivery device comprising a polymer film and a pharmaceutical active composition. In some embodiments, the pharmaceutical active composition is substantially thinner than the polymer film.

In some embodiments, delivery device 5 can be constructed by preparing a first wet polymer matrix and one or more of a permeation enhancer, pH adjusting buffer, taste masking agent, self-aggregating moiety (such as bentonite) and/or a flavor using a first solvent. A first wet film can be formed by casting the wet polymer matrix. The first wet polymer matrix can be deposited in a dryer apparatus and exposed to a temperature sufficient to flash off the first solvent to form a first dry film cast as a continuous single layer film laminate. A second wet solution or suspension comprising pharmaceutical active 20 (or a salt thereof) and optionally an oxygen scavenger and/or a drug solubilizer (such as a self-assembling phospholipid and/or bile salts) can then be prepared in a second solvent. A predetermined amount of the second wet solution or suspension can be applied on a surface (or onto selected areas of a surface) of the polymer film using spraying, electro-spraying, atomized coating, and/or ultra-thin web-coating processes. The wet multi-domain film can be deposited in a drying apparatus and exposed to a heating temperature sufficient to flash off the first and/or second solvents (e.g., about room temp to 250° C.) to form a dry continuous single layer pharmaceutical active-containing delivery device. In some embodiments, the pharmaceutical active composition is substantially thinner than the polymer film.

Delivery device 5 can be configured in any desired form, such as (but not limited to) film strips, sheets, discs, wafers, and the like. The delivery device can have any desired thickness, such as about 50 to about 500 μm, although films with greater or lesser thicknesses are included within the scope of the presently disclosed subject matter. Delivery device 5 can be configured in any desired shape, such as rectangular, square, rounded, triangular, abstract, and the like. It should be appreciated that delivery device 5 can have any desired thickness and/or size suitable for the intended use. For example, the delivery device can be a single-dosage sized unit that is to be placed into the oral cavity of the user.

Delivery device 5 can be formed from a continuous roll of film or can be sized to a desired length and width.

An exemplary embodiment of a pharmaceutical active-containing transmucosal delivery device includes a delivery device wherein the pharmaceutical active ingredient comprises nalmefene. The delivery device comprising nalmefene can be used for treatment of Prurigo Nodularis (PN) and Chronic Kidney Disease associated Pruritus (CKD-aP). Prurigo Nodularis is a chronic dermatologic condition characterized by severely pruritic nodules on the skin. Individuals suffering from Prurigo Nodularis usually have multiple excoriated lesions. This condition is common with patients suffering from chronic kidney disease, which results in a 'scratch-itch' cycle that forms discrete, nodular, excoriated, hyperpigmented/purpuric lumps with scaly or crusted surfaces. Varying dose strengths are contemplated. For example, dosage strengths may include 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 37.5 mg, 40 mg, 50 mg, 60 mg, 75 mg, 100 mg, 150 mg of nalmefene in a pharmaceutical active composition.

The excipients contemplated for use in the compositions have been used in existing commercial products and are in the FDA's inactive ingredient database. The excipients include; hydroxy propyl methylcellulose USP, polyethylene oxide NF, sodium carboxy methyl cellulose NF, sodium saccharin USP, sorbitol NF, blue FD&C dye, peppermint oil NF, monobasic sodium phosphate USP, dibasic sodium phosphate USP, PEG400 NF, glycerine USP, propylene glycol NF, ammonium glycyrrhizate NF, BRIJ® O2, ethanol NF and water NF.

Exemplary films can be packaged in white, opaque, individual sealed chevron pouches that are 2.5 inches wide and 3.5 inches long. Each pouch can include 1 piece of SteriFlex 301 foil that has been heat sealed to 1 piece of 301P foil. The films can be stored at room temperature at 25° C. The heat seal width can be 0.25 inches, which would require a peel strength force of between 0.6 to 3.0 pounds to open the pouch. The pouch is opened by cutting with scissors below the heat seal.

After removal from the pouch, the delivery device can be administered sublingually (under the tongue).

Unlike conventional oral film manufacturing, the active ingredient is not incorporated within the matrix of the polymer film or within the delivery device. Instead, the drug solution is either sprayed, or deposited directly onto the surface of the polymer film, which does not have active incorporated therein. Upon rapid evaporation of the solvent in which the active ingredient is dissolved (in the pharmaceutical active composition), a compositional quench takes place thereby causing the active to phase separate in the binding polymer without forming a nucleus.

Typical methods of creating nanoparticles are complex, expensive, and time consuming. The typical processes are multi-step and are often challenged by particle agglomeration concerns. The described method circumvents these concerns by using a single step process wherein nano- or microparticles are created using an application method that prevents agglomeration of pharmaceutical active during application and are then subsequently locked-in-place on the surface of the polymer film.

Advantageously, the described method can be scaled for commercial use. Offering single-step manufacturing significantly reduces the costs-of-goods. Moreover, the described method provides advantageous uniformity and consistency to the manufacturing process. The manufacturing method consistently produces delivery devices having a dosage that is within 90%-110% of the target dosage. For example, for a target dosage of 3.75 mg, delivery devices made using the described method will have a dosage within the range of 3.375 mg to 4.125 mg. Uniformity and consistency in the manufacturing process provides efficiency in production time and raw material usage thus leading to cost savings, increased profitability and reduced production time.

In use, the described delivery device comprising the pharmaceutical active can be administered to a subject in need thereof. For example, the disclosed film can be placed in contact with the oral mucosa of a subject. It should be appreciated that the manufacture of a single layer biocompatible film where the pharmaceutical active resides at a high concentration in a molecular state in the microenvironment in immediate proximity of the mucosa is critical to provide rapid transmucosal absorption of the pharmaceutical active. For such a system to work, the rate of dissolution of the pharmaceutical active must be significantly faster that the dissolution rate of the matrix. Further, such a device where the drug resides as a discrete high concentration domain will minimize salivary flow to the pharmaceutical active (akin to, but distinct from, a bi-layer film).

The disclosed film can provide effective taste masking, directional permeation, rapid absorption, and/or enhanced bioavailability of the pharmaceutical active. In some embodiments, the first discrete domain comprises a film-forming polymeric matrix, pH adjusting buffer, taste masking agent, self-assembling phospholipid or bile salts, and/or a flavoring agent to provide effective taste masking and/or directional permeation. In some embodiments, the first discrete film domain has slower rate of dissolution compared to the second discrete domain comprising pharmaceutical active 5.

Advantageously, the disclosed single-layer film structure includes a plurality of discrete domains, where the at least one of the discrete domains is rich in pharmaceutical active or its salts thereof.

Further, the presently disclosed subject matter includes single-layer film structures that comprise a plurality of discrete domains, wherein at least one of the domains is rich in pharmaceutical active or its salts thereof, and wherein the pharmaceutical active exists in a solid solution, amorphous, or monomorphic crystalline microparticle state.

The disclosed single-layer film structure further includes at least one discrete domain that provides effective taste masking and/or enhanced transmucosal absorption when the discrete domain comprising the pharmaceutical active is placed in contact with the oral mucosa of a subject.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Prophetic Example 1

Construction of Film Composition 1

Film composition 1 will be constructed by preparing a blend of a polymer and one or more excipients selected from hydroxy methyl cellulose USP, CARBOPOL® 971P NF, mannitol NF, sodium saccharin, phosphotidyl choline, glycerol dioleate, colorant, citric acid, and orange flavor. The blend will be solubilized and the components dispersed in water. The blend will then be cast into wet film of a defined thickness on a release liner surface, such as LOPEREX®. Upon controlled drying at 60° C. for 20 minutes in a convection oven, the film will be dry and the phosphotidyl choline and glycerol dioleate will have self-assembled at the film surface. As a result, a single layer film with two domains will be constructed. A pharmaceutical active (such as scopolamine) and a pH adjusting buffer (such as citric acid) will be incorporated on the surface of the polymer film by spray atomization, creating a third domain on the surface of the film. The film product will be cut into individual disc units devices of about 1.14 cm$^2$.

Prophetic Example 2

Construction of Film Composition 2

Film composition 2 will be constructed by preparing a blend of a polymer and one or more excipients selected from hydroxy propyl methyl cellulose USP, CARBOPOL® 971P NF, mannitol NF, sodium saccharin NF, phosphotidyl glycerol, colorant, and peppermint flavor. The blend will be solubilized and dispersed in water. The blend will then be cast into wet film of a defined thickness on a release liner surface, such as LOPEREX®. Upon controlled drying at 160° C. for 12 minutes in a convection oven, a film comprising a polymer film will be constructed. A predetermined amount of a pharmaceutical active agent (such as Asenapine HCl USP, CARBOPOL® 971P NF, NOVEON® Polycarbophil AA-1 NF, and sodium citrate NF) will be sprayed on the surface of the polymer film, creating a pharmaceutical active composition. The pharmaceutical active composition represents a predetermined amount of pharmaceutical active (Asenapine HCl USP) deposited as a spray on the surface of the polymer film. The film product will be cut into individual disc units devices of 2.6 cm$^2$.

Prophetic Example 3

Construction of Film Composition 3

Film composition 3 will be constructed by preparing a blend of a polymer and one or more excipients selected from hydroxy propyl methyl cellulose USP, sodium saccharin NF, sodium benzoate NF, FD&C colorant, citric acid, mannitol NF, and lemon mint flavor. The blend will be solubilized and dispersed in water. The blend will then be cast into wet film of a defined thickness on a release liner surface, such as LOPEREX®. Upon controlled drying at 120° C. for 15 minutes in a convection oven, a film comprising a polymer film will be constructed. A predetermined amount of a pharmaceutical active will be deposited as a spray on the surface of the polymer film, creating a pharmaceutical active composition. The pharmaceutical active will comprise treprostinil USP, vitamin E acetate, NOVEON® Polycarbophil AA-1 NF, and sodium citrate NF. The film product will be cut into individual disc units devices of 2.6 cm$^2$.

Prophetic Example 4

Construction of Film Composition 4

A single layer film with two domains will be created by producing a wet polymer blend of hydroxy propyl methyl cellulose USP, sodium saccharin NF, phosphotidyl choline, PECEOL®, vitamin E acetate, sodium benzoate NF, FD&C colorant, LYCASIN® maltitol 80/55, lemon flavor and water. The polymer blend will be cast at a predefined thickness onto a LOPEREX® release liner of approximately 1 mm wet thickness, and will be subsequently dried at 60° C. for 30 minutes to form a first dry film.

A second wet drug solution comprising a predetermined amount of pharmaceutical active, nalmefene HCl USP, vitamin E acetate, NOVEON® Polycarbophil AA-1 NF, citric acid, and sodium citrate NF will be prepared. The resulting film will be dried for 10 minutes at 95° C. in a convection oven. The film product will be cut into individual disc units devices of 1.14 cm$^2$.

Example 5

Pharmaceutical Active Ingredient Solubility

Figure 3:
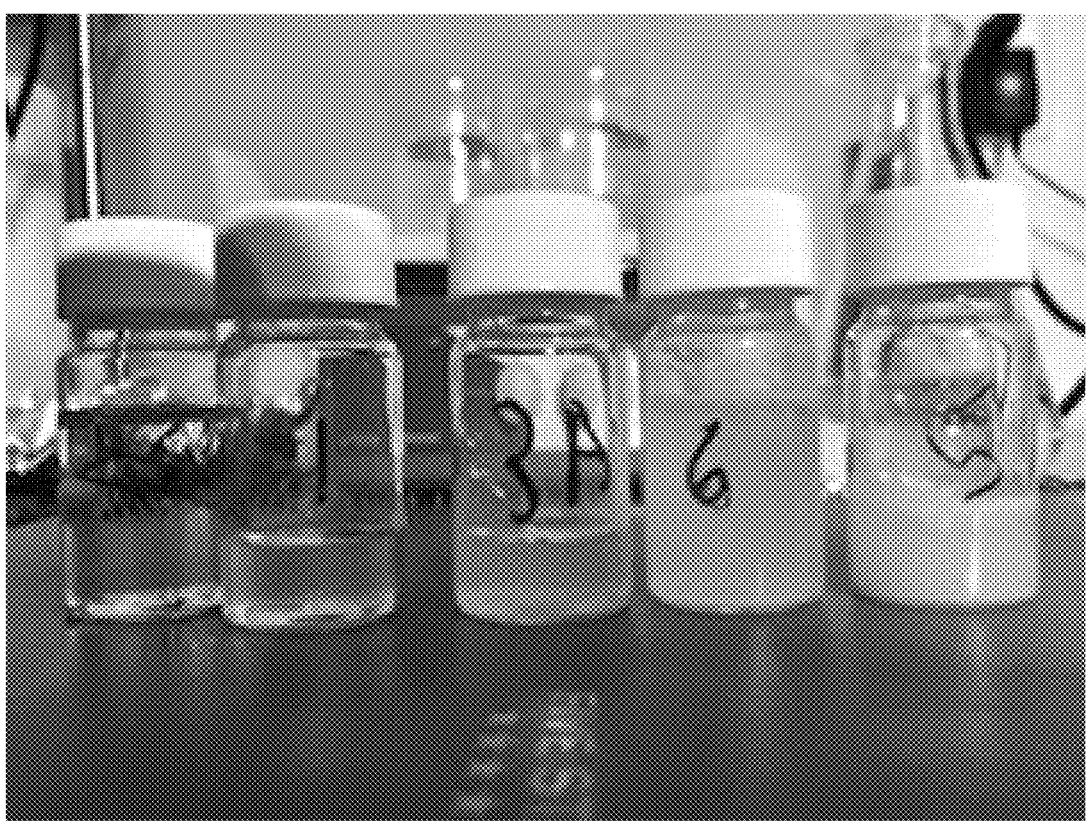
FIG. 3 is a photograph showing solubility of nalmefene as a function of pH in accordance with Example 5.
Figure 4:
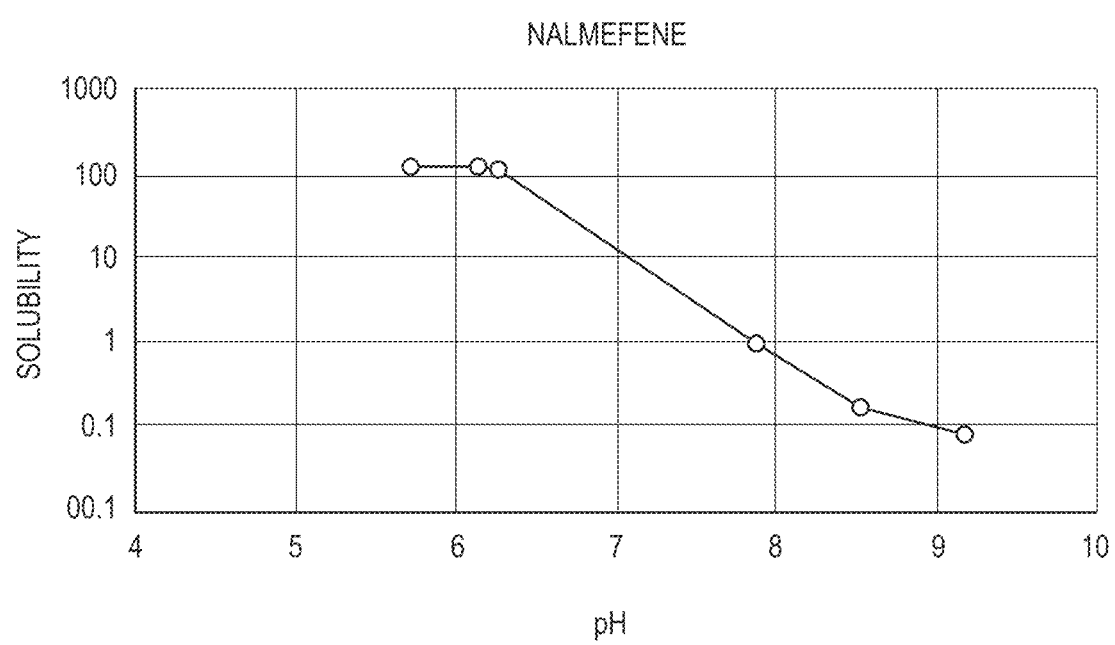
FIG. 4 is a chart illustrating Merck's Index solubility data of nalmefene at different pH conditions.

To determine the solubility of an exemplary pharmaceutical active ingredient, a visual assessment study (mimicking cloud point) was performed at five different pH conditions—pH 2.25, 4.0, 6.8, 8.0, 9.6 with 100 mg/mL. The exemplary pharmaceutical active ingredient was nalmefene (expressed as a free base). Experiments were conducted to determine the cloud point. FIG. 3 is a photograph of samples at the five tested pH levels. As shown, FIG. 3 illustrates the cloud point at various tested pH levels. From left to right, the pH of the aqueous media increased. An observed cloud point at 6.8 (vial 3A) demonstrated the solubility inflexion pH, which is consistent with data presented in the Merck Index, 19th Edition, (2001) for the exemplary pharmaceutical active ingredient. A chart of the solubility data provided in the Merck Index is shown in FIG. 4.

Example 6

Pharmaceutical Active Ingredient Solubility

Testing was performed to evaluate the solubility of an exemplary pharmaceutical active ingredient in solubility enhancing polar solvents and solubilizing agents. The exemplary active was nalmefene HCL monohydrate at 100 mg/mL. The different solvents that were considered included ethanol, propylene glycol, glycerol, methanol, and water. Table 1 shows the solubility evaluation observations.

TABLE 1

Solubility of Nalmefene in Polar Solvents

| Polar Solvent | Solubility of Nalmefene HCl Monohydrate | Test Concentration (mg/mL) |
| --- | --- | --- |
| Ethanol NF | Partially | 100 |
| Propylene glycol USP | Partially | 100 |
| Glycerol USP | Partially | 100 |
| Methanol | Highly | 100 |
| Water NF | Moderately high | 100 |

In addition, the solubility of nalmefene in varying concentrations was evaluated using different combinations of solvent systems. The solvent systems included combinations of polar solvents with different surface active agents. Exemplary surface active agents included: Tween 20, Tween 80, GELUCIRE® 34/44, KOLLIPHOR® HS 15, SOLUTOL® NF, LABRAFIL® M2125 CS and LABRAFIL® M1944 CS.

Table 2 shows the solubility evaluation observations.

| ID | Solvent System | Ratio | Nalmefene Concentration (mg/mL) | Observation |
| --- | --- | --- | --- | --- |
| 1 | Ethanol:Water | 75:25 | 200 | Completely Soluble, pale yellowish beige |
| 2 | Ethanol:Water:Tween 20 | 75:24.5:0.5 | 250 | Completely Soluble, pale yellowish beige |
| 2 | Ethanol:Water:Propylene Glycol | 82.5:12.5:5 | 200 | Completely Soluble, colorless to pale beige |
| 3 | Ethanol:Water:Propylene Glycol | 68:22:10 | 350 | Completely Soluble, yellowish beige |
| 5 | Ethanol:Water:Propylene Glycol:Tween 80 | 70:25:4:1 | 350 | Completely Soluble, yellowish beige |
| 6 | Ethanol:Water:Glycerine | 70:20:10 | 300 | Completely Soluble, yellowish beige |
| 7 | Ethanol:Water:Gelucire 34/14 | 75:20:5 | 200 | Completely Soluble, pale yellowish beige |
| 8 | Ethanol:Water:Labrafil M2125 CS | 80:17.5:2.5 | 200 | Completely Soluble, pale yellowish beige |
| 9 | Ethanol:Water:Labrafil M1944 CS | 80:17.5:2.5 | 200 | Completely Soluble, pale yellowish beige |

Example 7

Buffering Agents for Use with Pharmaceutical Active Compositions

Figure 5:
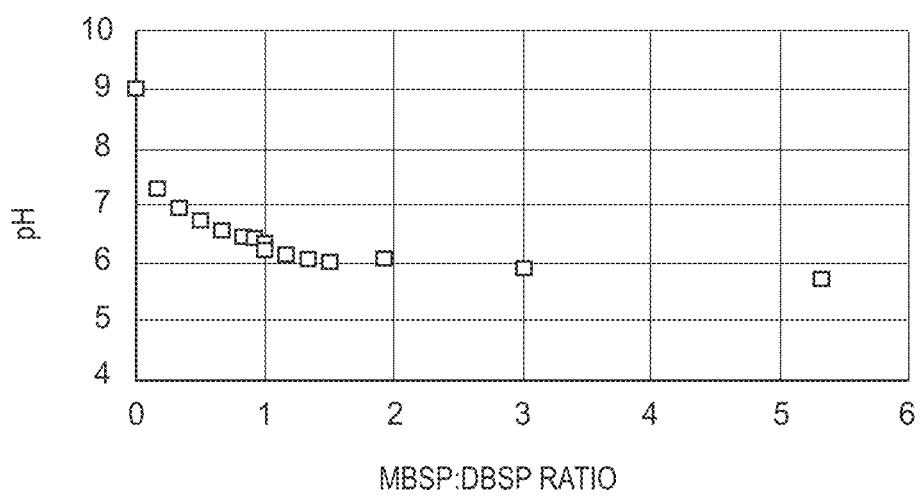
FIG. 5 is a chart illustrating the buffering capacity of combinations of monobasic sodium phosphate and dibasic sodium phosphate at varying ratios.

Testing was performed to evaluate buffer combinations for controlling pH of an exemplary pharmaceutical active composition in a range from 5.75 to 9. Combinations of monobasic sodium phosphate and dibasic sodium phosphate in varying concentration ratios were tested. The results are shown in FIG. 5.

Figure 6:
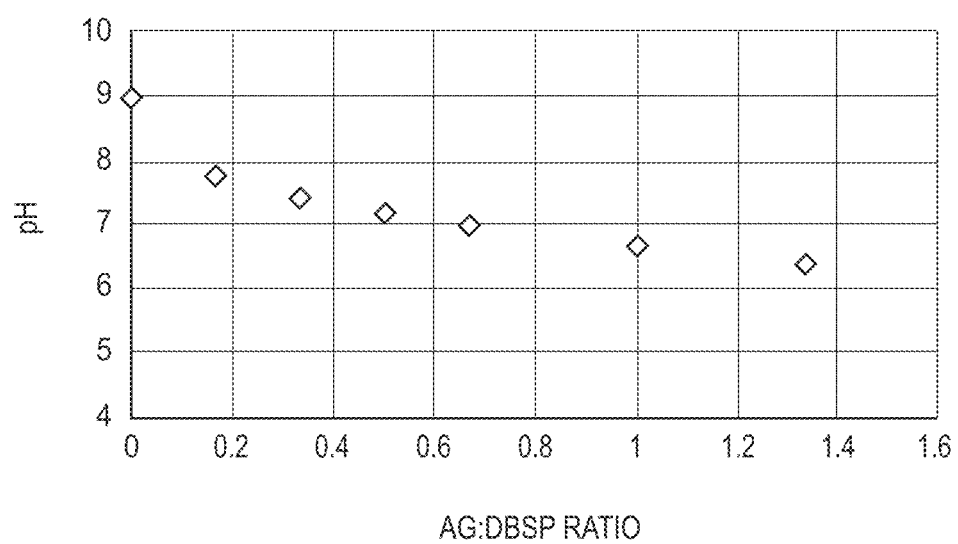
FIG. 6 is a chart illustrating the buffering capacity of the combination of ammonium glycyrrhinate-dibasic sodium phosphate at varying ratios.

Moreover, it was determined that ammonium glycyrrhinate, which is more conventionally used as a taste masking agent, can be used in combination with dibasic sodium phosphate as a suitable buffering agent in a buffering range between 6.25 and 9. FIG. 6 is a graph showing pH control of exemplary buffering agent combinations that include combinations of ammonium glycyrrhinate and dibasic sodium phosphate in varying ratios. As can be seen, the combinations provided pH control at relatively high pH conditions. The buffer combination of ammonium glycyrrhinate and dibasic sodium phosphate can be used to control pH at higher pH conditions, such as 7.5 or higher.

Example 8

Considering Excipients for Pharmaceutical Active Compositions

Exemplary compositions including varying components were considered and evaluated. Varying anticrystallization agents for reducing and/or preventing nucleation and growth of the active in an oral film dosage form were considered.

Additionally, excipients affecting residence time in the mouth with suitable mucoadhesive and pH attributes were considered. Residence times may range from about 5 minutes to about 30 minutes, such as for example about 8 minutes to about 10 minutes. Additionally, divalent calcium ions that instantaneously gel sodium alginate thereby preventing active migration into the polymer film was tested. Moreover, different flavoring agents and/or taste masking agents were tested.

Exemplary formulations having varying selections of polymers, molecular weights, and polymer ratios were prepared. Additionally, exemplary formulations were prepared having varying selections and amounts of flavoring agents, coloring agents, taste masking agents, sweeteners, plasticizers, humectants, bioenhancers, and buffering agents.

A summary of components, amounts, and compositional relationships for exemplary compositions is provided in Table 3.

| Functionality | Exemplary Ingredient | Amount Range (mg) | Compositional Relationship |
|---|---|---|---|
| Drug | Nalmefene HCl monohydrate | 1 to 75 mg | 10 to 90% of drug in the delivery device composition, 20% concentration or higher at the surface of the film |
| Anticrystallization agent(s) (AC) | Sorbitol, mannitol | 0.5 to 25 mg | Ratio range of AC agent:drug of 1:1.5 to 1:20 |
| Polymer(s) | Aqualon NaCMC, Low and medium MW PEO, and Low and Medium MW HPMC | 25 to 250 mg | 10 to 90% of polymer in the delivery device composition |
| Bioenhancer, | docusate sodium USP and Brij O2 | 0.1 to 15 mg | <5% in the delivery device composition |
| pH adjusting agent(s) | monobasic sodium phosphate, dibasic sodium phosphate, ammounium glycyrhhirinate | .5 to 20 mg | <5% in the delivery device composition |
| Salt gelling agent | Calcium chloride, USP | .05 to 5 mg | <2% in the delivery device composition, calcium choride:sodium alginate ratio ranges from 1:10 to 10:1 |
| Barrier polymer | Sodium Alginate, NF | 0.1 to 50 mg | <2% in the delivery device composition |
| Additional excipients | Peppermint Oil, Blue FD&C, sodium saccharrin, glycerin | 0.2 to 50 mg | <1 to 20% in the delivery device composition |

Additional exemplary compositions using different drug concentrations are shown below in Table 4.

| Material | Functionality | Example 1 weight (mg) | Example 2 weight (mg) | Example 3 weight (mg) |
|---|---|---|---|---|
| Nalmefene HCl monohydrate | Drug | 4.350 | 8.700 | 17.415 |
| Sorbitol, NF | Anticrystallization agent | 5-10 | 5-10 | 5-10 |
| Mannitol NF | Anticrystallization agent | 0.01-1 | 0.01-1 | 0.01-1 |
| Glycerin, USP | plasticizer | 5-10 | 5-10 | 5-10 |
| Docusate sodium USP or Brij O2 | bioenhancer | 0.01-1 | 0.01-1 | 0.01-1 |
| Peppermint Oil, NF | flavor | 1-10 | 1-10 | 1-10 |
| Blue FD&C | colorant | 0.01-1 | 0.01-1 | 0.01-1 |
| HPLC, Vivapharm E5, NF | Polymer binder | 0.1-2 | 0.1-2 | 0.1-2 |
| Calcium chloride, USP | Salt gelling agent | 0.01-1 | 0.01-1 | 0.01-1 |
| Polyox N10 | Polymer binder | 0.1-2 | 0.1-2 | 0.1-2 |
| Benecel HPMC K100LV | Film Forming Polymer | 10-60 | 10-60 | 10-60 |
| Aqualon NaCMC 7L2P | Mucoadhesive Polymer | 10-60 | 10-60 | 10-60 |
| Sodium Alginate, NF | Barrier Polymer | 0.01-1 | 0.01-1 | 0.01-1 |

| Material | Functionality | Example 1 weight (mg) | Example 2 weight (mg) | Example 3 weight (mg) |
|---|---|---|---|---|
| Sodium Saccharin, USP | Sweetener | 0.5-3 | 0.5-3 | 0.5-3 |
| Polyethylene glycol 400, NF | Plasticizer | 0.5-3 | 0.5-3 | 0.5-3 |
| Monobasic sod phosphate, anhydrous | pH adjusting buffer | 0.5-3 | 0.5-3 | 0.5-3 |
| Dibasic Sod. Phosphate, USP | pH adjusting buffer | 0.5-3 | 0.5-3 | 0.5-3 |
| Total | | 90-120 | 90-120 | 90-120 |

Example 9

Dissolution and Ex Vivo Permeation Testing

Figure 7:
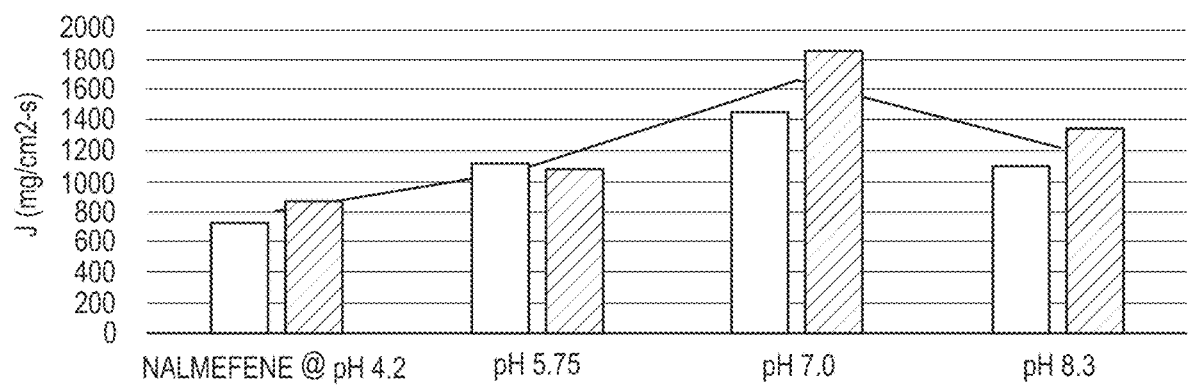
FIG. 7 is a chart comparing ex vivo porcine buccal flux when using exemplary embodiments of the delivery device described herein in comparison to conventionally available nalmefene at a pH of 4.2.

Dissolution and ex vivo permeation was tested at varying pH conditions, including pH values of 5.75, 7.0, and 8.3. Exemplary delivery devices comprising nalmefene HCl monohydrate were tested. The compositions of the delivery devices were the same except for the pH, which was varied. The delivery devices at varying pH were tested in comparison to a Nalmefene tablet at pH value of 4.2. Two samples were tested for each exemplary device and for the reference tablet. Ex-vivo porcine buccal mucosa was considered and used in a buccal mucosa Franz-cell following EMA/CHMP/QWP/608924/2014, and OECD-Guideline 28 and 428 Guideline for the testing of chemicals, skin absorption—in vitro Method. The results are shown in FIG. 7. As can be seen in FIG. 7, the permeability for each of the delivery devices was higher than that for the reference, with the delivery device having a pH of 7.0 having the highest permeability.

What is claimed is:

1. A method of manufacturing a pharmaceutical active-containing transmucosal delivery device comprising
blending a polymer matrix and a pH adjusting agent;
solubilizing the blend;
casting the blend into a wet polymer film;
drying the polymer film;
applying a pharmaceutical active composition onto a surface of the polymer film, wherein a viscosity of the pharmaceutical active composition is from about 1 cP to about 100 cP; and
heating the polymer film with the pharmaceutical active composition applied thereto in order to form the pharmaceutical active-containing transmucosal delivery device,
wherein the active pharmaceutical composition is not a self-supporting layer and is embedded within the polymer film after the heating has occurred;
wherein the formed pharmaceutical active-containing transmucosal delivery device is a single unit dose device.

2. The method of manufacturing of claim 1, wherein applying the pharmaceutical active composition comprises applying the pharmaceutical active composition onto the surface of the polymer film by droplet deposition, spraying, ultrasonic atomizer, atomized coating, and/or ultra-thin web-coating processes onto the polymer film.

3. The method of manufacturing of claim 2, wherein the viscosity of the pharmaceutical active composition is from about 1 cP to about 50 cP.

4. The method of manufacturing of claim 2, wherein heating the polymer film with the pharmaceutical active composition applied thereto is performed at a temperature ranging from about 50° C. to about 150° C.

5. The method of manufacturing of claim 2, wherein heating the polymer film with the pharmaceutical active composition applied thereto is performed for about 3 minutes to about 10 minutes.

6. The method of manufacturing of claim 1, wherein applying the pharmaceutical active composition comprises dropwise deposition of the pharmaceutical active composition on the surface of the polymer film.

7. The method of manufacturing of claim 6, wherein the viscosity of the pharmaceutical active composition is from about 20 cP to about 100 cP.

8. The method of manufacturing of claim 6, wherein a temperature of the polymer film when drops of the pharmaceutical active composition are deposited thereon ranges from about 90° C. to about 150° C.

* * * * *